(12) United States Patent
Rohland et al.

(10) Patent No.: US 8,999,044 B2
(45) Date of Patent: Apr. 7, 2015

(54) GAS CHROMATOGRAPHY INLET LINER HAVING A COLORED REGION

(76) Inventors: Edmund C. Rohland, Vineland, NJ (US); Glen R. Campbell, Rockaway, NJ (US)

(*) Notice: Subject to any disclaimer, the term of this patent is extended or adjusted under 35 U.S.C. 154(b) by 271 days.

(21) Appl. No.: 13/373,873

(22) Filed: Dec. 2, 2011

(65) Prior Publication Data

US 2012/0204621 A1 Aug. 16, 2012

Related U.S. Application Data

(60) Provisional application No. 61/458,956, filed on Dec. 3, 2010.

(51) Int. Cl.
 *B01D 53/02* (2006.01)
 *G01N 30/60* (2006.01)
 *G01N 30/16* (2006.01)

(52) U.S. Cl.
 CPC ............... *G01N 30/16* (2013.01); *G01N 30/60* (2013.01)

(58) Field of Classification Search
 USPC ............................................. 96/101, 105–17
 See application file for complete search history.

(56) References Cited

U.S. PATENT DOCUMENTS

| | | | | | |
|---|---|---|---|---|---|
| 2,434,139 | A | * | 1/1948 | Armistead | 501/56 |
| 4,035,168 | A | * | 7/1977 | Jennings | 73/864.85 |
| 5,119,669 | A | * | 6/1992 | Silvis et al. | 73/23.41 |
| 5,439,593 | A | * | 8/1995 | Price | 210/660 |
| 5,472,670 | A | * | 12/1995 | Harrington et al. | 422/89 |
| 5,610,107 | A | * | 3/1997 | Danielson et al. | 501/54 |
| 5,954,862 | A | * | 9/1999 | Wilson | 96/101 |
| 5,997,615 | A | * | 12/1999 | Luong et al. | 96/105 |
| 6,203,597 | B1 | * | 3/2001 | Sasano et al. | 95/87 |
| 6,494,939 | B1 | * | 12/2002 | Tipler | 96/105 |
| 6,498,042 | B1 | * | 12/2002 | Wilson | 436/174 |
| 6,565,634 | B1 | * | 5/2003 | van Egmond | 96/105 |
| 6,719,826 | B2 | * | 4/2004 | Sasano et al. | 95/87 |
| 6,974,495 | B2 | * | 12/2005 | Tipler et al. | 96/105 |
| 7,105,043 | B2 | * | 9/2006 | O'Neil | 96/101 |
| 7,350,427 | B2 | * | 4/2008 | Sandra et al. | 73/863.23 |
| 7,384,457 | B2 | * | 6/2008 | Emmons et al. | 96/106 |
| 8,366,814 | B2 | * | 2/2013 | Jones et al. | 96/105 |
| 8,713,989 | B2 | * | 5/2014 | Pa et al. | 73/23.39 |
| 2005/0229723 | A1 | * | 10/2005 | Bremer et al. | 73/864.81 |
| 2009/0249959 | A1 | * | 10/2009 | Jones et al. | 96/106 |
| 2013/0081484 | A1 | * | 4/2013 | Jones et al. | 73/864.91 |

OTHER PUBLICATIONS

Gas Chromatograph Liner Sample Pack Request, SGE Analytical Science, available on the Internet Archive on Sep. 28, 2010.*
K. Grob, "Split and Splitless Injection for Quantitative Gas Chromatography", Wiley-VCH, 2001, pp. 120-146.
K. Grob and M. Biedermann, "The Two Options for Sample Evaporation in Hot GC Injectors: Thermospray and Band Formation. Optimization of Conditions and Injector Design", Anal. Chem. 2002, pp. 10-16.
W.A. Weyl, "Coloured Glasses", Society of Glass Technology, 1959.
K. Grob and M. Biedermann, "The Two Options for Sample Evaporation in Hot GC Injectors: Thermospray and Band Formation. Optimization of Conditions and Injector Design", Anal. Chem. 2002, pp. 10-16.
W.A. Weyl, "Coloured Glasses", Society of Glass Technology, 1959.

*Primary Examiner* — David A Rogers (57) ABSTRACT

A liner for mixing the sample gas and a carrier gas and delivering the gas mixture to the inlet end of a capillary tube of a gas chromatograph for analysis, comprises
(a) a transparent tube having an inlet and an outlet and a bore with an inside surface, and
(b) at least one glass subcomponent permanently affixed to the liner tube wherein the subcomponent is at least one color.

11 Claims, 6 Drawing Sheets

GAS CHROMATOGRAPHY INLET LINER HAVING A COLORED REGION

FIELD OF THE INVENTION

This invention relates to injection ports for capillary gas chromatographs, and more particularly concerns liner units for inlets wherein a liquid sample is vaporized into a sample gas and mixed with a carrier gas, and a portion of the gas mixture is delivered to the inlet end of a capillary tube of a gas chromatograph, and even more particularly concerns marking such liners to identify the type and source of the liners and to provide proper orientation of the liner in the gas chromatography instrument.

DESCRIPTION OF THE PRIOR ART

Gas chromatography (GC) is a well known analytical technique where gas phase mixtures are separated into their individual components and subsequently identified. The technique may be employed to obtain both qualitative and quantitative information about the components of the mixture [1].

Samples for GC are usually liquid and must be vaporized prior to introduction to the mobile phase gas stream. GC analysis is typically divided into four stages:
1. sample introduction, where liquid samples are introduced into the inlet, heated, and vaporized,
2. sample transfer, where the sample vapor is transferred all or in part onto the analytical column,
3. separation, where the sample is separated into its individual components as it passes through the analytical column, and
4. detection, where the separated components are identified as they exit the analytical column.

In conventional GC instrumentation the first two steps are achieved in the sample inlet hardware. Inlet hardware often includes a replaceable liner. Liners are normally operated at elevated temperatures, e.g., over 200° C. This enhances the rate of sample vaporization and reduces adsorption on the inner surface of the liner [1]. Many internal configurations are available for liners, as well as coatings for them [2-12].

In most cases the configuration serves to enhance the degree of sample vaporization from the point of exit from the syringe needle to the column entrance, and provide gas phase sample homogeneity of components within the liquid mixture having different boiling points. A simple configuration for an inlet liner is a straight cylindrical tube of glass having a consistent inner diameter along the longitudinal path. Other configurations include more complex inner paths intended to increase turbulence, affect the comparatively short residence time the liquid sample is in the liner, or interrupt the liquid stream leaving the syringe needle. These internal configurations include tapers or goosenecks, baffles, funnels, inverted cup elements, spiral regions, and other points of flow constriction along the longitudinal path of the liner.

Other optional elements of liners include small quantities of packing materials such as glass wool [1] or Carbofrit™ (Trademark of Restek Corporation) packing material, which serve as additional surface area sources for heat transfer into the sample and as a physical filter for any solid/nonvolatile contaminants present in the liquid sample.

Liners are manufactured from glass, primarily borosilicate, but also fused quartz, and less commonly from metal, mainly stainless steel [13]. Various chemical coatings are applied to liners in order to reduce the degree of interaction between the sample and the surface of the liner. Sample-surface interactions may result in sample adsorption in the coatings, decomposition of the coatings, and formation of new reaction products; in each case resulting in undesirable peaks (or loss of desirable ones) in detection measurements of the components contained in the sample being analyzed in the separation analysis. In addition to low sample-surface interactions, it is also desirable for the liner coating to be thermally stable in order to minimize background signal contributions originating from the liner coating itself detected by the analytical equipment. For glass substrate liners, common deactivation techniques include chemically treating the exposed silanol groups with organosilane reagents such as hexamethyldisilazane (HMDS), dimethyldichlorosilane (DMCS), and trimethylchlorosilane (TMCS) [13]. Prior to the deactivation process it is common for the liner substrate to undergo an aqueous acid leach process [13] whereby metal and metalloid impurities are removed from the surface.

It is often desirable for the liner to be optically transparent. It is particularly important to be able to see through the walls of these liners which contain packing material in order to ensure its proper plug position within the internal bore of the liner. It is also advantageous to be able to observe wool placement, and to be able to check for the presence of debris or other visual contaminants. For the purpose of this disclosure we will reference to liners that are manufactured from glass or other optically transparent materials.

Given the large number of GC instrument manufacturers, different instrument models, and considerable variety of liner designs, it is desirable to include markings on the liners that provide information relating to the variables listed above. It is further desirable to provide information relating to proper orientation of the liner in the GC instrument.

Information specific to liners is often provided by directly marking the liners with text, symbols, or logos. Methods for marking include silk screening or direct stamp printing on the outer surface of the liners. Marks are made on the surface using paint or ink, as well as mechanical and chemical etching techniques. These techniques, while widely used in the industry are often limited in their long term thermostability as well as their overall ease of visibility given the narrow dimensions of standard liners (e.g., on the order of 2-6 mm O.D.). Further, these techniques require additional steps in the liner manufacture, and may impact the subsequent chemical deactivation process following the mechanical forming of the glass substrate.

With the exception of the straight liner, which is essentially a straight glass tube having a uniform I.D and O.D. along the entire length, liners having more complex internal configurations are commonly manufactured by (1) heat fusing subcomponents to the inner surface of the straight tubing, or (2) thermoforming the outer wall of the straight tubing to create complex shapes on the inner wall. In the first case, glass subcomponents whose chemical compositions are compatible to the straight tubing are employed in order to ensure thorough fusing of the parts. In most cases the chemical composition of the subcomponents is essentially the same as the straight tube.

In some cases, more than one subcomponent is employed in the same straight tube. In still other cases, more than one subcomponent is employed where the first subcomponent resides inside the second subcomponent in a coaxial configuration.

SUMMARY OF THE INVENTION

We present an alternative to directly printing or otherwise marking the liner by taking advantage of the multicomponent nature of the liner assembly. We present replacing one or more of the liner subcomponents with dimensionally equivalent subcomponents made from pigment doped glass, the pigment for such glass preferably comprising inorganic pigments. In this fashion the liners whole or in part include a discreet colored region that is highly visible and can be employed to identify one liner from another or identify proper orientation in the GC instrument.

The liner unit at least comprises a tube having a bore extending between an inlet and outlet of the tube, but may also comprise an inlet expansion chamber in the bore for changing a liquid sample into a sample gas, a mixing chamber in the bore next to the inlet chamber, and an outlet chamber for delivering the thoroughly mixed sample and carrier gases to an inlet end of a capillary tube of a gas chromatograph. Employing one or more colored glass subassemblies of the liner during its manufacture enables easier identification of the liner type, proper orientation, or identification of the source of the liner.

Because of the techniques used in liner manufacture, any pigment employed in the glass subcomponents must be resistant to temperatures greater than the softening point of borosilicate glass (ca. 650° C.), and more preferably greater than the softening point of quartz (ca. 1650° C.). Inorganic ionic pigments such as cobalt ($Co^{+2}$; blue color), nickel ($Ni^{+2}$; green color) and iron ($Fe^{+2}$; yellow to red color) are commonly employed as thermostable pigments in glass substrates [14] and are suitable examples for this application.

Employing a color doped subcomponent in the liner assembly provides a striking device to identify the liner without adding any steps beyond those essential to the liner manufacture. Preferably, the pigment concentrations in the glass liner subcomponents are sufficient to provide a noticeable color while maintaining optical transparency of the liner.

Employing pigment-doped glass for liner subcomponents allows for close melt compatibility between the doped and non-doped subcomponents. In the final assembly of the liner some of the glass surface of the subcomponent may be exposed to the sample path. Because the liner substrate undergoes an aqueous acid leach process prior to the deactivation process, inorganic pigment ions resident at or close to the surface of the colored glass would be removed and a higher purity silica surface would be presented to the deactivation chemistry.

BRIEF DESCRIPTION OF THE DRAWINGS

FIG. 3A-1 is a view in cross-section of a cylindrical gooseneck subassembly of the invention.

FIG. 3A-2 is an end view of the cylindrical gooseneck subassembly shown in FIG. 3A-1.

FIG. 3B-1 is a view in cross-section of an alternative embodiment of a cylindrical gooseneck subassembly of the invention.

FIG. 3B-2 is an end view of the cylindrical gooseneck subassembly shown in FIG. 3B-1.

FIG. 3C-1 is a view in cross-section of another alternative embodiment of a cylindrical gooseneck subassembly of the invention.

FIG. 3C-2 is an end view of the cylindrical gooseneck subassembly shown in FIG. 3C-1.

DETAILED DESCRIPTION

FIG. 1 shows some liner configurations commonly found in the industry.

Figure 1A:
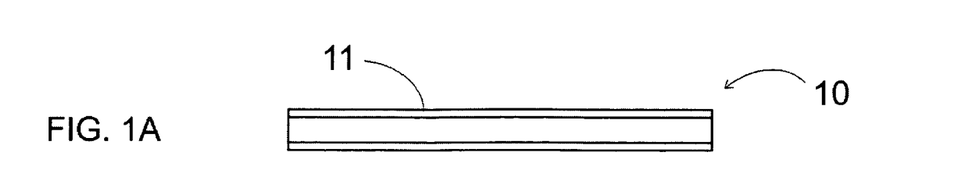
FIG. 1A is a view in cross-section of a liner found in the prior art.
Figure 1B:
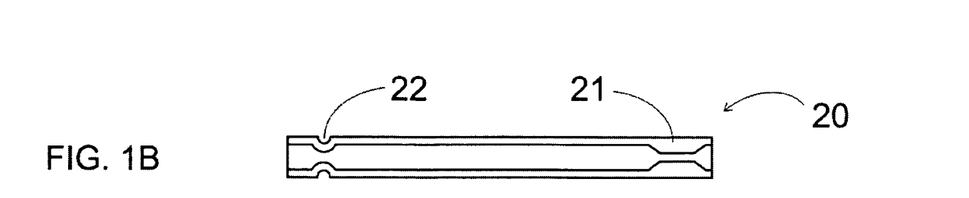
FIG. 1B is a view in cross-section of another liner found in the prior art.
Figure 1C:
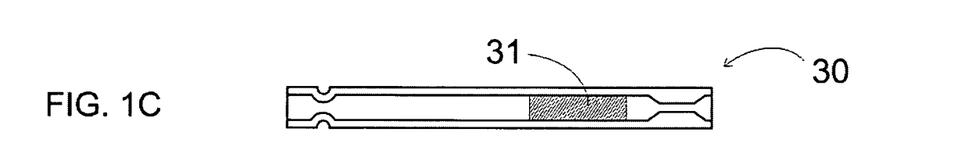
FIG. 1C is a view in cross-section of another liner found in the prior art.
Figure 1D:
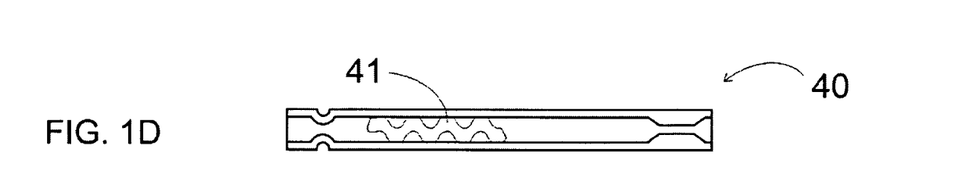
FIG. 1D is a view in cross-section of another liner found in the prior art.

In FIGS. 1A-1D, sectional views of various sample inlet liner configurations are illustrated as known in the prior art. FIG. 1A is an example of a straight through sample inlet liner 10 having a straight tube wall 11. FIG. 1B shows a liner 20 which is an example of the liner 10 incorporating a gooseneck taper 21 where the taper region has a reduced inner diameter and the same outer diameter of the straight liner tube wall 11. The liner 20 also has a dimple 22 which is a region of the liner 20 having both a reduced inner diameter and outer diameter. FIG. 1C shows a liner 30 which is an example of the liner 20 incorporating a matrix 31, which may be comprised of wool, particles, wire bundles, or other materials know in the art. FIG. 1D shows a liner 40 which is an example of a Cyclosplitter.TM. liner [5] which includes the physical features of liner 20 and also includes a glass spiral core baffle 41 permanently affixed to the inner surface of the liner 40.

Figure 2A:
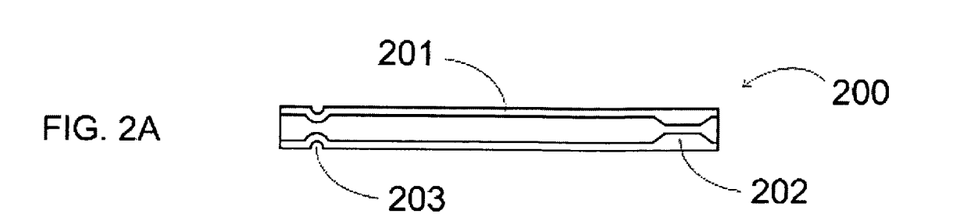
FIG. 2A is a view in cross-section of a sample inlet liner having a gooseneck taper and a dimple, constructed in accordance with the invention.
Figure 2B:
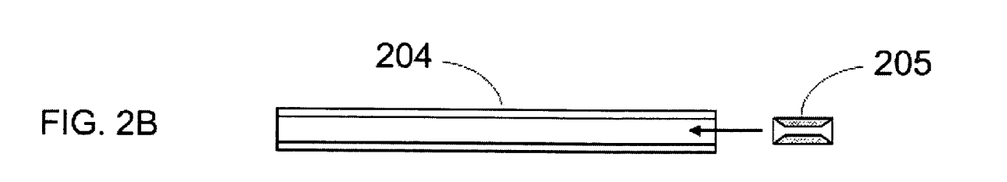
FIGS. 2B and 2C are views in cross-section illustrating the fabrication of the gooseneck liner of FIG. 2A.
Figure 2C:
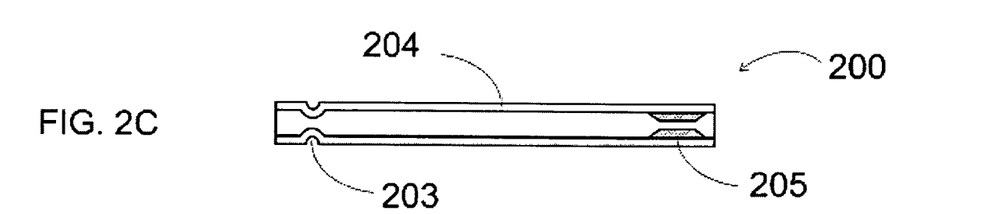

FIG. 2A is a sectional view of an inventive sample inlet liner 200 incorporating a gooseneck taper 202 where the taper region has a reduced inner diameter and the same outer diameter of the straight liner tube wall 201 and a dimple 203 which is a region of the liner 200 having both a reduced inner diameter and outer diameter. In FIGS. 2B to 2C the fabrication of the gooseneck liner 202 is illustrated. As shown in FIG. 2B, a glass subassembly 205 is inserted into the straight tube 204 and permanently heat fused into place. In this particular case the glass subassembly 205 is made of colored glass. With the exception of the glass pigment, the chemical composition of the subassembly 205 is preferably the same material as the liner tube 204. This improves the physical and chemical compatibility between the two components and ensures successful fusing of the components together. In FIG. 2C the dimple 203 is shown to be added after heat fusing the gooseneck taper into place. Common manufacturing practices to create the dimple include thermoforming, whereby the straight tube 204 is heated in a localized region to at least the softening point of the glass and then pinched into place. Often the straight tube 204 is rotated along the longitudinal axis in order to ensure a symmetrical dimple around the radial axis of the tube 204. In commercial manufacture of liners the order of the steps illustrated here may be changed.

Figure 3A:
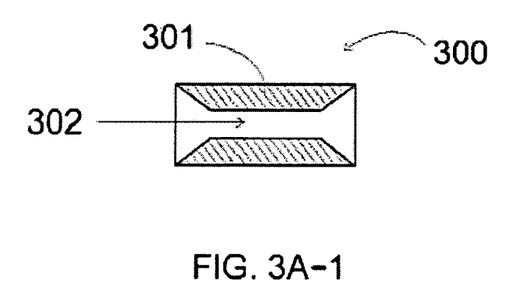
Figure 3A:
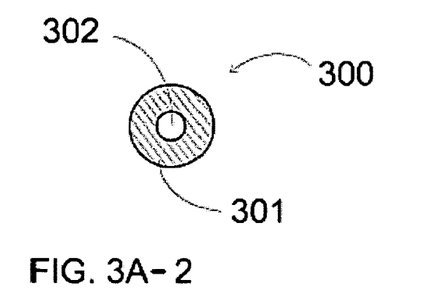
Figure 3B:
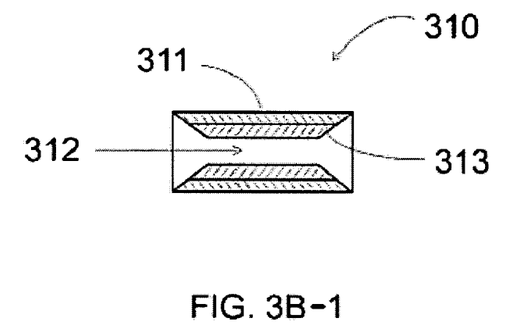
Figure 3B:
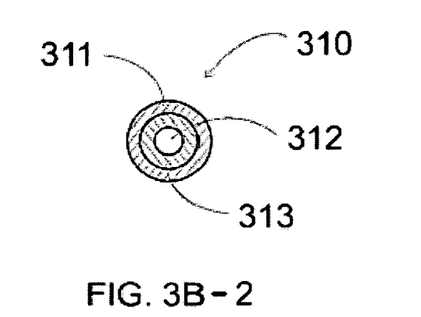
Figure 3C:
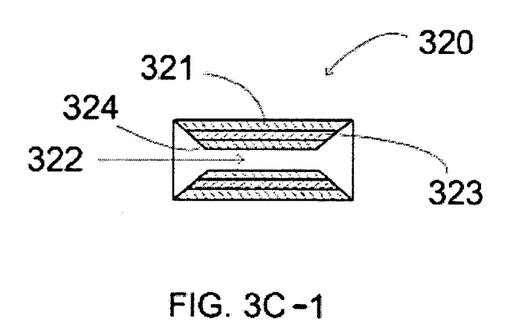
Figure 3C:
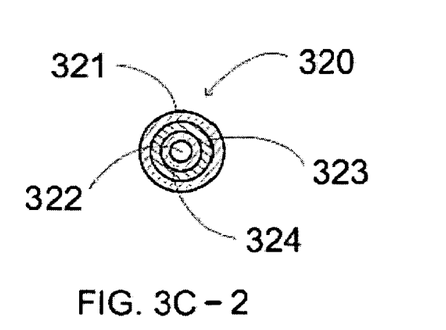

FIG. 3A-1 is a detail illustration of a cylindrical gooseneck subassembly 300 having a through channel 302. The subassembly is made of colored glass, preferably colored borosilicate glass. FIG. 3A-2 shows an end view of the subassembly 300 of FIG. 3A-1. Both ends of the gooseneck are chamfered giving the cross section profile 301. FIG. 3B-1 is a detail illustration of a cylindrical gooseneck subassembly 310 having a through channel 312. FIG. 3B-2 shows an end view of the subassembly 310 of FIG. 3B-1 where the subassembly is made of one cylindrical layer of glass 313 surrounded by a second cylindrical layer of glass 311, assembled in a coaxial configuration where the cumulative shape is equivalent to the single component gooseneck subassembly 300. In this example either layer 313 or layer 311 or both contain color pigment. In the case where both layer 313 and 311 contain color pigment, they may be the same or different color. At some point during the manufacture of the liner, subassemblies 313 and 311 are fused together. FIG. 3C-1 is a detail illustration of a cylindrical gooseneck subassembly 320 having a through channel 322. FIG. 3C-2 shows an end view of the subassembly 320 where the subassembly is made of one cylindrical layer of glass 324 surrounded by a second cylindrical layer of glass 323, which is in turn surrounded by another cylindrical layer of glass 321 assembled in a coaxial configuration where the cumulative shape is equivalent to the single component gooseneck subassembly 300. In this example any of the three layers 324, 323 or 321 may contain color pigment. In the case where any of the three layers 324, 323 or 321 contain color pigment, they may be the same or different color. At some point during the manufacture of the liner, the three layers 324, 323 and 321 are fused together.

Figure 4A:
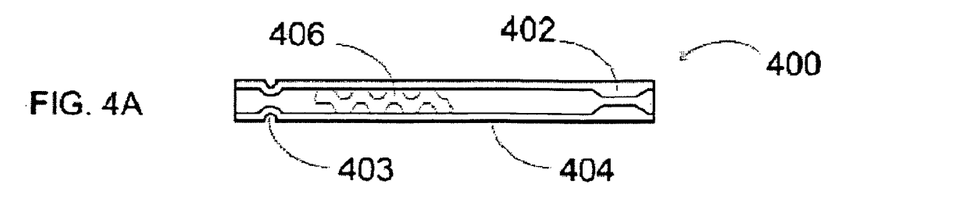
FIG. 4A is a view in cross-section of a Cyclosplitter™ liner constructed in accordance with the invention.

FIG. 4A shows a Cyclosplitter™ liner 400, which is constructed in accordance with the invention, and which incorporates a gooseneck taper 402 where the taper region has a reduced inner diameter and the same outer diameter of the straight liner tube wall 404, and a dimple 403 which is a region of the liner 400 having both a reduced inner diameter and outer diameter. The Cyclosplitter™ liner 400 also incorporates a glass spiral core baffle 406 permanently affixed to the inner surface of the liner.

Figure 4B:
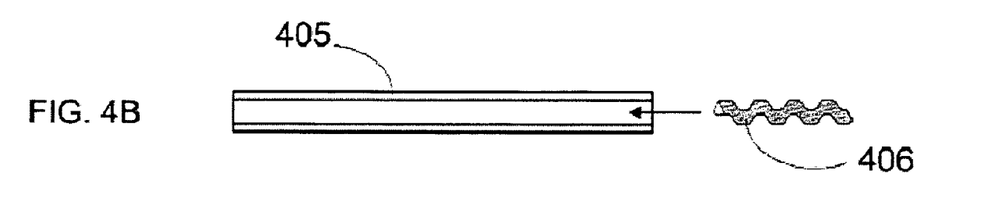
FIGS. 4B, 4C, and 4D are views in cross-section illustrating the fabrication of the liner of FIG. 4A.
Figure 4C:
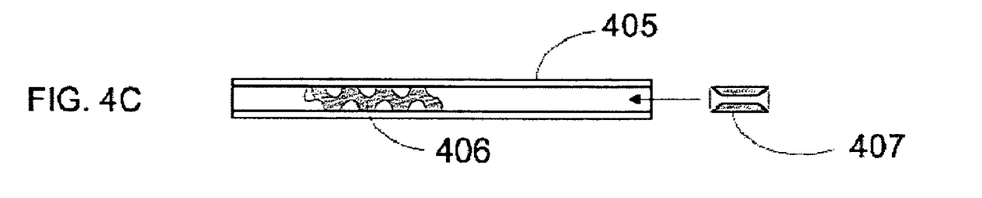
Figure 4D:
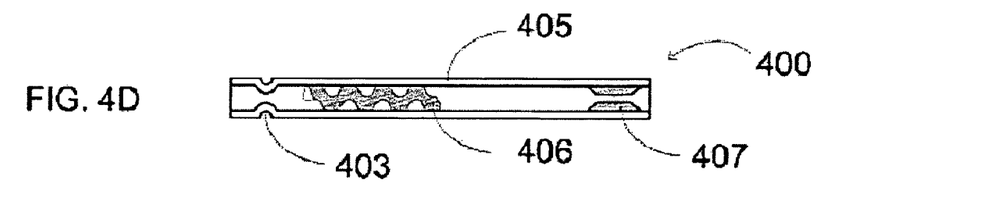

In FIGS. 4B to 4D, the fabrication of the Cyclosplitter™ liner 400 is illustrated. In FIG. 4B, a glass spiral core baffle subassembly 406 is inserted into the straight tube 405 and permanently heat fused into place. In this particular case the core baffle subassembly 406 is made of colored glass. With the exception of the glass pigment, the chemical composition of the subassembly 406 is preferably the same material as the liner tube 405. This improves the physical and chemical compatibility between the two components and ensures successful fusing of the components together. In FIG. 4C the gooseneck taper subassembly 407 is inserted into the straight tube 405 and permanently heat fused into place. In this particular case the glass subassembly 407 is made of colored glass. With the exception of the glass pigment, the chemical composition of the subassembly 407 is preferably the same material as the liner tube 405. The color of spiral core baffle subassembly 406 may be the same as or different to the gooseneck taper subassembly 407. In FIG. 4D the dimple 403 is applied to liner tube 405 in the same fashion as described previously. In commercial manufacture of liners the order of the steps illustrated here may be changed.

Figure 5A:
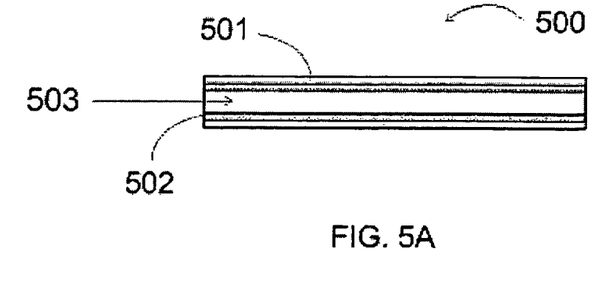
FIG. 5A is a view in cross-section of an alternative embodiment of a liner constructed in accordance with the invention.
Figure 5B:
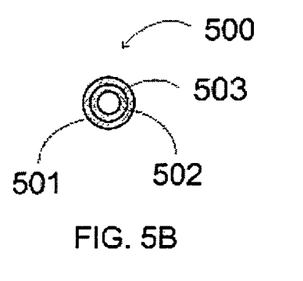
FIG. 5B is an end view of the liner shown in FIG. 5A.

FIGS. 5A to 5G show straight liners having colored regions along the longitudinal path of the straight tube. Liners in FIGS. 5A to 5G are made of glass, preferably borosilicate glass. The glass subassemblies are heat fused together. In FIG. 5A a straight tube liner 500 having a through hole or pathway 503 includes a clear glass sheath 501 and a colored glass sheath 502 which are assembled in a coaxial fashion. FIG. 5B shows an end view of the final assembly of liner 500.

Figure 5C:
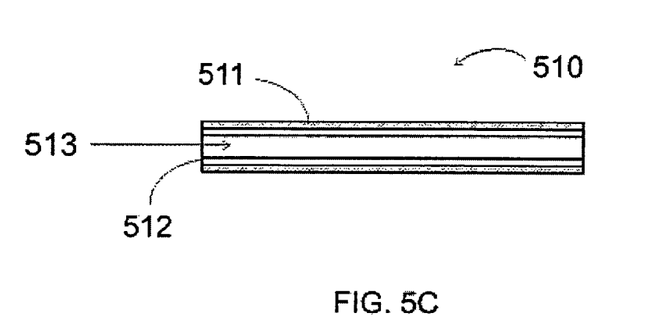
FIG. 5C is a view in cross-section of another alternative embodiment of a liner constructed in accordance with the invention.

In FIG. 5C the liner 510, having a through hold or pathway 513, is assembled with the colored glass sheath 511 on the outside of the clear glass sheath 512. This configuration is preferable when the chemical composition of the colored sheath 511 is sufficiently different from the clear glass 512 as to be potentially less compatible with either the deactivation chemistry or the gas sample.

Figure 5D:
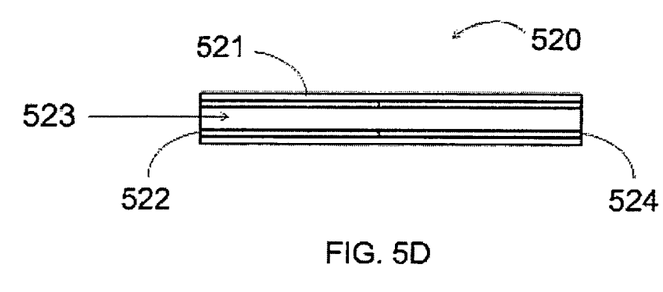
FIG. 5D is a view in cross-section of another alternative embodiment of a liner constructed in accordance with the invention.

In FIG. 5D the straight tube liner 520 having a through hole or pathway 523 includes two separate colored sheaths 522 and 524 inserted coaxially into the straight tube 521 where the total length of the two colored sheaths 522 and 524 matches the length of the straight tube 521. In this case the colored sheaths 522 and 524 may be the same color or different colors.

Figure 5E:
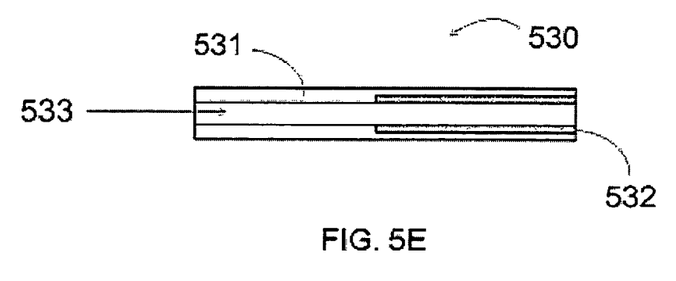
FIG. 5E is a view in cross-section of a further alternative embodiment of a liner constructed in accordance with the invention.

In FIG. 5E the straight tube liner 530 having a through hole or pathway 533 includes a clear sheath 531 and a colored sheath 532 where the length of colored sheath 532 is less than the length of clear sheath 531. In order to ensure an even inner diameter along the entire length of the liner 530, the glass tube 531 may be thicker in the region without the colored sheath 532.

Figure 5F:
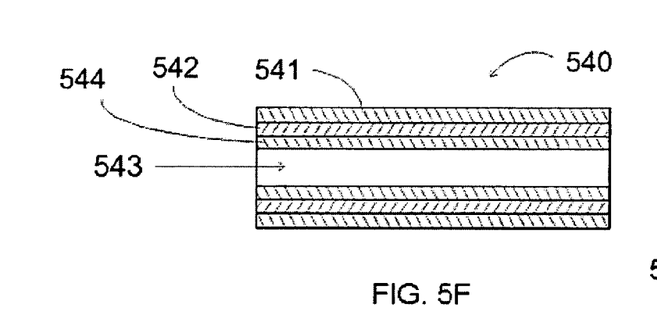
FIG. 5F is a view in cross-section of another alternative embodiment of a liner constructed in accordance with the invention.
Figure 5G:
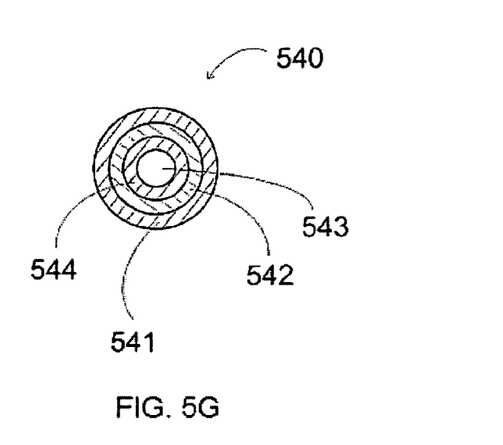
FIG. 5G is an end view of the liner shown in FIG. 5F.

In FIG. 5F the straight tube liner 540 having a through hole or pathway 543 includes three glass sheaths 541, 542, and 544 which are assembled in a coaxial fashion. FIG. 5G shows an end view of the final assembly of liner 540. Any or all of the glass sheaths 541, 542, and 544 may be colored and more than three sheaths may be included in the liner assembly. As was illustrated in FIG. 5C, any of the glass sheaths 541, 542, and 544 may be composed of more than one shorter glass sheath assembled end to end where the total length of the sheaths matches the length of the straight tube.

The glass sheaths in each of FIGS. 5A to 5G are fused together, preferably by heat fusing.

Pigment may be added to any or all of the glass components (e.g., glass subassemblies 205, 300, and 407, glass layers 311, 313, 321, 323, and 324, glass spiral core baffles 406, and glass sheaths 502, 511, 522, 524, 531, 541, 542, and 544) of the inventive liners, as desired, using conventional methods known to those of ordinary skill in the art, such as by mixing pigment into the glass melt from which the glass components are formed.

The references referred to in this specification and listed below are hereby incorporated herein by reference.

REFERENCES

1. Konrad Grob in "Split and Splitless Injection for Quantitative Gas Chromatography, 4$^{th}$ Ed., Wiley-VCH, 2001.
2. *Anal. Chem.* 2002, 74, 10-16 "The Two Options for Sample Evaporation in Hot GC Injectors: Thermospray and Band Formation. Optimization of Conditions and Injector Design" Koni Grob and Maurus Biedermann.
3. U.S. Pat. No. 5,954,862 "Sample Inlet Liner" William H. Wilson.
4. U.S. Pat. No. 5,472,670 "Gas Chromatography Sample Injector and Apparatus Using Same" Peter de B. Harrington and Hans P. Whittenberg.
5. U.S. Pat. No. 5,119,669 "Sleeve Units for Inlet Splitters of Capillary Gas Chromatographs" Paul H. Silvis.
6. U.S. Pat. No. 6,565,634 "Injection Liner" Wil van Egmond.

7. U.S. Pat. No. 6,719,826 "Method and Apparatus for Sample Injecting in Gas Chromatography" Ryoichi Sasano, Motoaki Satoh, and Yutaka Nakanishi.
8. U.S. Pat. No. 6,498,042 "PTFE Matrix in a Sample Inlet Liner and Method of Use" William H. Wilson.
9. U.S. Pat. No. 4,035,168 "Nonreactive Inlet Splitter for Gas Chromatography and Method" Walter G. Jennings.
10. U.S. Pat. No. 5,997,615 "Large-Sample Accessory for a Gas Chromatograph" Huan V. Luong, Hsing Kuang Lin, Howard Fruwirth, George S. Mueller.
11. U.S. Pat. No. 6,203,597 "Method and Apparatus for Mass Injection of Sample" Ryoichi Sasano, Kazuhiko Yamazaki, Masahiro Furuno.
12. U.S. Pat. No. 6,494,939 "Zero-Dilution Split Injector Liner Gas Chromatography" Andrew Tipler.
13. "A Guide To Gas Chromatography", W. Rodel and G. Wolm, Huthig Verlag, GmbH, Heidelberg, Germany.
14. "Coloured Glasses" by W. A. Weyl, 1959, Society of Glass Technology, Sheffield.

We claim:

1. A liner for mixing a sample gas and a carrier gas and delivering the gas mixture to the inlet end of a capillary tube of a gas chromatograph for analysis, comprising:
   (a) a transparent tube having an inlet and an outlet and a bore forming an inside tube surface, and
   (b) at least one glass subcomponent permanently affixed to the transparent tube wherein the subcomponent is at least one color, wherein the glass subcomponent comprises a first cylinder aligned coaxial with the transparent tube permanently affixed to the inside tube surface of the transparent tube and a second cylinder positioned in a bore of the first cylinder.

2. The liner of claim 1, wherein the subcomponent comprises an inorganic pigment.

3. The liner of claim 2, wherein the inorganic pigment is thermostable at temperatures in excess of the softening point of borosilicate glass.

4. The liner of claim 2, wherein the inorganic pigment is thermostable at temperatures in excess of the softening point of quartz.

5. The liner of claim 2, wherein the inorganic pigment is selected from the group consisting of cobalt, nickel, and iron.

6. The liner of claim 1, wherein the first cylinder is chamfered.

7. The liner of claim 1, wherein the second cylinder is chamfered.

8. The liner of claim 1, wherein the first and second cylinders each contain an inorganic pigment.

9. The liner of claim 8, wherein the first and second cylinders each contain a different inorganic pigment.

10. The liner of claim 1, wherein the glass subcomponent comprises an inorganic pigment and wherein, except for the inorganic pigment, the glass subcomponent and the transparent tube have substantially the same chemical composition.

11. A liner for mixing a sample gas and a carrier gas and delivering the gas mixture to the inlet end of a capillary tube of a gas chromatograph for analysis, comprising:
   (a) a transparent tube having an inlet and an outlet and a bore forming an inside tube surface, and
   (b) at least one glass subcomponent permanently affixed to the transparent tube wherein the subcomponent is at least one color, wherein the glass subcomponent comprises a first chamfered cylinder permanently affixed to the inside tube surface of the transparent tube and a second chamfered cylinder positioned in a bore of the first chamfered cylinder.

* * * * *